United States Patent [19]

Harreus et al.

[11] Patent Number: 5,739,400
[45] Date of Patent: Apr. 14, 1998

[54] PREPARATION OF O-(2-HYDROXYALKYL) OXIMES

[75] Inventors: Albrecht Harreus, Ludwigshafen; Norbert Götz, Worms; Harald Rang, Altrip, all of Germany

[73] Assignee: BASF Aktiengesellschaft, Ludwigshafen, Germany

[21] Appl. No.: 776,579

[22] PCT Filed: Jul. 25, 1995

[86] PCT No.: PCT/EP95/02932

§ 371 Date: Feb. 3, 1997

§ 102(e) Date: Feb. 3, 1997

[87] PCT Pub. No.: WO96/04237

PCT Pub. Date: Feb. 15, 1996

[30] Foreign Application Priority Data

Aug. 2, 1994 [DE] Germany ............... 44 27 290.1

[51] Int. Cl.$^6$ .............................. C07C 249/12
[52] U.S. Cl. .............................. 564/256
[58] Field of Search ........................ 564/256

[56] References Cited

U.S. PATENT DOCUMENTS 3,040,097 6/1962 Bachman et al. ............... 564/256
4,064,186 12/1977 Gibson et al. ................. 260/618

FOREIGN PATENT DOCUMENTS 023 560 6/1980 European Pat. Off. .
44 15 887 5/1994 Germany .

OTHER PUBLICATIONS

Houben–Weyl, *Methods of Organic Chemistry*, vol. 6/3, 4th Edition 1965, pp. 442–446.
Bouzoubaa et al., *J. of Med. Chem.*, vol. 27, No. 10, Oct. 1984, pp. 1291–1294.

*Primary Examiner*—Peter O'Sullivan
*Attorney, Agent, or Firm*—Keil & Weinkauf

[57] ABSTRACT

Preparation of O-(2-hydroxyalkyl)oximes I

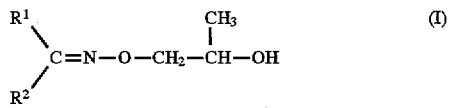

($R^1$ and $R^2$=alkyl or $R^1$ and $R^2$ and the C atom which carries them=5- to 7-membered cycloalkyl), by catalytically hydrogenating an O-(2,3-epoxyalkyl)oxime of the general formula II

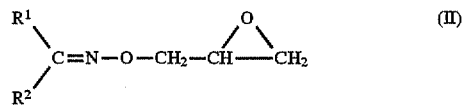

using hydrogen.

The products I are suitable as intermediates for herbicides.

4 Claims, No Drawings

PREPARATION OF O-(2-HYDROXYALKYL) OXIMES

This application is a 371 of PCT/EP95/02932 Jul. 25, 1995.

The present invention relates to a process for preparing O-(2-hydroxyalkyl)oximes of the general formula I

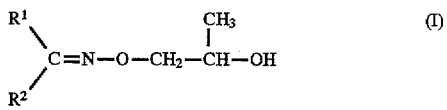

where $R^1$ and $R^2$ are each alkyl groups having 1 to 10 carbon atoms or, together with the carbon atom which carries them, are bonded to give a 5- to 7-membered cycloalkyl radical.

O-(2-Hydroxyalkyl)oximes are of great importance as intermediates for crop protection agents (cf. eg. the earlier German Application DE-A 44 15 887).

In the preparation of compounds of the type I by O-alkylation of hydroxylamines, to a certain extent the compound isomeric to I which carries the $CH_3$ group on the C atom which is adjacent to the oxime oxygen is also always formed.

The previously described hydrogenations of oxiranes lead either to the primary alcohol or to a mixture of secondary and primary alcohol (cf. eg. U.S. Pat. No. 4,064,186 and Houben-Weyl, Methoden der Organischen Chemie [Methods of Organic Chemistry], Georg Thieme Verlag, Stuttgart, Vol. 6/3, 4th Edition, 1965, pages 442–446).

It is an object of the present invention to provide a process which leads with higher regioselectivity and substantially without formation of by-products to the O-(2-hydroxyalkyl) oximes I.

We have found that this object is achieved by a process for preparing the O-(2-hydroxyalkyl)oximes of the formula I, which comprises catalytically hydrogenating an O-(2,3-epoxyalkyl)oxime of the general formula II

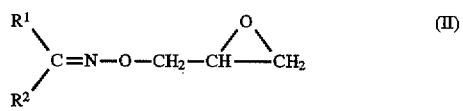

using hydrogen.

In the following, the Houben-Weyl literature references relate to: Houben-Weyl, Methoden der Organischen Chemie (Methods of Organic Chemistry), 4th Edition, Thieme Verlag, Stuttgart.

Among the compounds I which can be prepared by the process according to the invention, those are preferred in which $R^1$ and $R^2$ each are a $C_1$-$C_4$-alkyl group and especially a $C_1$-$C_3$-alkyl group, or, together with the carbon atom which carries them, form a cyclopentyl or cyclohexyl ring. Particularly preferably, $R^1$ and $R^2$ are each methyl or ethyl, in particular both methyl.

The O-(2,3-epoxyalkyl)oximes II are generally known or are obtainable by known methods, especially by base-catalyzed reaction of the corresponding epihalohydrins with the free oximes in a dipolar aprotic solvent (cf. eg. Zh. Org. Khim. 5 (1969), page 1353 to page 1355).

Suitable catalysts for the hydrogenation are catalysts generally customary for this purpose, as are described e.g. in Houben-Weyl, Volume 4/1c.

Preferred hydrogenation catalysts are those which comprise a metal from groups 8 to 10 according to the IUPAC classification of the Periodic Table, preferably from the group consisting of the elements cobalt, ruthenium and rhodium, especially from the group consisting of the elements platinum and nickel, and in particular palladium.

The catalysts can be used as such or preferably on a support. Customary support materials such as silica, alumina, titanium dioxide, silicates and zeolites and especially activated carbon are suitable.

For preparation of the supported catalysts binders or shaping aids can be additionally used. The catalysts can be employed in the form of chips, extrudates, tablets or balls.

In general, 0.1 to 2, preferably 0.1 to 1%, by weight of catalyst are employed per mole of the compound II to be hydrogenated, these quantitative data relating to the active mass of the catalyst without support materials.

The hydrogenation can be carried out continuously or, preferably, batchwise.

In batchwise procedure in the liquid phase, the hydrogenation can be carried out in the presence of a solvent. Suitable solvents are polar solvents such as ethers and alcohols as well as mixtures thereof. Preferred solvents are ethers or alcohols having up to 6 carbon atoms such as 1,2-dimethoxyethane, ethanol, n-propanol, isopropanol and n-butanol.

The pressure can be selected within wide limits which extend from 1 to 400 bar, but the reaction is preferably carried out in a pressure range from 1 to 100, especially from 10 to 70 and in particular from 30 to 50 bar.

The temperature during the hydrogenation is preferably 0 to 100, especially 10 to 50 and in particular 25° to 30° C.

The reaction products I are isolated by methods known per se, preferably by distillation. The yield of the compounds I is normally from 70 to 90%, with a selectivity of, as a rule, over 98%.

The O-(2-hydroxyalkyl)oximes I obtainable by the process according to the invention are suitable as precursors for herbicides, in particular of the cyclohexenone type (cf. eg. DE-A 44 15 887).

EXAMPLE

Preparation of 2-propanone O-(2-hydroxypropyl) oxime 130 g (0.94 mol) of 2-propanone O-(2-epoxypropyl) oxime (cf. EP-A 23 560; Zh. Org. Khim. 5 (1969), pages 1353 to 1355) and 600 ml of ethanol were treated with 4 g of palladium/carbon (10% by weight palladium) and the mixture was hydrogenated at 25° C. and a hydrogen pressure of 50 bar. After 17 hours the reaction was complete. The catalyst was filtered off. The solvent was then removed and the residue was distilled through a packed column of length 50 cm and diameter 5 cm, which was packed with wire mesh rings of diameter 3 mm (b.p.: 74° C./20 mbar).

The yield of 2-propanone O-(2-hydroxypropyl)oxime was 84%, with a purity of 99.8%. Isomeric 2-propanone O-(2-hydroxy-1-methyl-ethyl)oxime was not formed in this case.

We claim:

1. A process for preparing O-(2-hydroxyalkyl)oximes of the general formula I

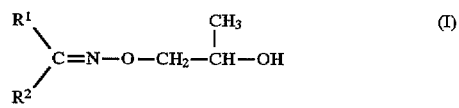

where $R^1$ and $R^2$ are each alkyl groups having 1 to 10 carbon atoms or, together with the carbon atom which carries them, are bonded to give a 5- to 7-membered cycloalkyl radical, which comprises catalytically hydrogenating an O-(2,3-epoxyalkyl)oxime of the general formula II

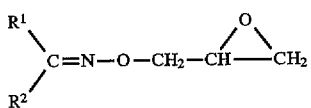 (II)
using hydrogen.
2. A process as claimed in claim 1, wherein the starting material used is an O-(2,3-epoxyalkyl)oxime where $R^1$ and $R^2$ are methyl.
3. A process as claimed in claim 1, wherein the catalyst used is an element of groups 8 to 10 of the Periodic Table.
4. A process as claimed in claim 1, wherein the catalyst used is palladium, if desired on a support.
* * * * *